United States Patent [19]

Loomstein

[11] Patent Number: 4,933,362
[45] Date of Patent: Jun. 12, 1990

[54] SUNBURN TREATMENT COMPOSITION

[76] Inventor: Jack Loomstein, 9740 Bonhomme Estates Dr., Olivette, Mo. 63132

[21] Appl. No.: 363,045

[22] Filed: Jun. 6, 1989

[51] Int. Cl.⁵ .............................................. A61K 31/40
[52] U.S. Cl. ................................................... 514/420
[58] Field of Search ...................... 424/59, 60; 514/420

[56] References Cited

U.S. PATENT DOCUMENTS 4,440,777  4/1984  Zupan ..................................... 424/59

FOREIGN PATENT DOCUMENTS 1574302  6/1977  United Kingdom .

*Primary Examiner*—Douglas W. Robinson
*Assistant Examiner*—Kevin E. Weddington
*Attorney, Agent, or Firm*—Gravely, Lieder & Woodruff

[57] ABSTRACT

A composition for reducing heat and pain and preventing blistering in humans suffering from sunburn comprising indomethacin, benzocaine, and phenol in an aqueous alcoholic base.

7 Claims, No Drawings

SUNBURN TREATMENT COMPOSITION

BACKGROUND OF THE INVENTION

This invention relates to the treatment of sunburns in particular, relates to a composition for providing relief from the heat and pain of sunburn while also providing protection from infection and preventing blistering.

A principal object of the present invention is to provide a composition and method for treating sunburn which provides relief for the heat and pain of the sunburned skin and also provides protection from infection and prevents blistering.

Still another object is to provide a composition for treating a sunburn which has a combination of indomethacin, benzocaine, and phenol in a base of ethyl alcohol and water.

A further object of this invention is to provide a composition having the aforesaid ingredients which will provide analgesic and antiseptic qualities to sunburned skin such that the heat and pain is dissipated within 6-8 hours after application locally to the skin.

These and other objects and advantages will become apparent hereinafter.

SUMMARY OF THE INVENTION

This invention comprises a composition and method of topically treating sunburn to reduce redness and pain which includes indomethacin, benzocaine and phenol in a liquid base.

DETAILED DESCRIPTION

The present invention includes indomethacin, 1-(p-Chlorobenzoyl)-5-methoxy-2-methylindole-3-acetic acid, in an amount of from about 0.04% to about 2% by weight. Preferably the composition contains about 0.083% indomethacin by weight. The indomethacin is dissolved in ethyl alcohol and has a solubility of about 1 gram/50 ml ethyl alcohol. The purpose for the indomethacin is to reduce the heat and soreness of the skin resulting from over exposure to sunlight. Three articles reported in the 1970's discuss the effect of indomethacin on sunburned skin. These are Intradermal Anti-prostaglandin Agents and Sunburn by Snyder and Eaglstein, *The Journal of Investigative Dermatology*, Vol. 62, No. 1, pg. 47-50, 1974; The Influence of Corticosterords and Topical Indomethacin on Sunburn Erythema by Kaulbey and Kurban, The *Journal of Investigative Dermatology*, Vol. 66, No. 3, pg. 153-156, 1976; and Topical Indomethacin and Sunburn by Snyder and Eaglstein, *British Journal of Dermatology*, pg. 90-91, 1974.

The composition also includes from about 0.25 to about 1% benzocaine or ethyl aminobenzoate ($C_9H_{11}NO_2$) by weight of the composition. The ethyl aminobenzoate is used for its anesthetic qualities to reduce the pain of the sunburn when applied locally. The preferred amount of ethyl aminobenzoate is 0.5% by weight. The ethyl aminobenzoate has a long lasting anesthetic effect.

From about 0.5% to about 2% by weight phenol ($C_6H_6O$) is in the composition. The preferred amount of phenol is about 1% by weight. The phenol is an antiseptic and has a quick acting anesthetic effect on the burned skin.

The indomethacin and the benzocaine, preferably, are dissolved in ethyl alcohol. The solubility of the indomethacin is 1gm/50ml, and the solubility of the benzocaine is 1gm/5ml of alcohol.

The phenol is in its liquid form and will dissolve in water or ethyl alcohol.

EXAMPLE NO. 1

The preferred composition comprises:

| | |
|---|---|
| Indomethacin | 0.083% by weight |
| Benzocaine | 0.5% by weight |
| Phenol (liquid) | 1.0% by weight |
| Ethyl alcohol | 4 cc |
| Distilled $H_2O$ | 60 cc |

In making the preferred composition, the indomethacin and benzocaine are dissolved in ethyl alcohol. The phenol is added to the water and the resulting mix is added to the ethyl alcohol mixture. The composition preferably is applied by a spray pump bottle. The application is complete when the red/burn area is totally wet from the spray.

EXAMPLE NO. 2

| | |
|---|---|
| Indomethacin | 0.083% by weight |
| Phenol (liquid) | 1.0% by weight |
| Ethyl alcohol | 12 cc |
| 10% soln. potassium hydroxide | 0.5 cc |
| Distilled $H_2O$ | 60 cc |

This composition does not include benzocaine. The ethyl alcohol is increased to 12 cc and 0.5 cc of a 10% solution of potassium hydroxide is added to the composition. The purpose of the potassium hydroxide is to adjust pH and effect solubility. The amount can be between about 0.5 cc to about 1. cc. Even though it does not contain benzocaine, the phenol in the composition still reduces the pain from sunburn.

EXAMPLE NO. 3

| | |
|---|---|
| Indomethacin | 0.083% by weight |
| Benzocaine | 0.5% by weight |
| Phenol (liquid) | 1.0% by weight |
| Dioctyl sodium sulfosuccinate | 0.025% |
| Ethyl alcohol | 5 cc |
| 10% KOH soln. | 0.25 cc |
| Distilled $H_2O$ | 60 cc |

In this Example No. 3, the ethyl alcohol and KOH is reduced. The benzocaine is combined with a surfactant, i.e., dioctyl sodium sulfosuccinate (DSS). The DSS serves to allow the indomethacin and the benzocaine to dissolve more quickly and completely.

EXAMPLE NO. 4

| | |
|---|---|
| Indomethacin | 0.083% by weight |
| Phenol (liquid) | 1.0% by weight |
| Ethyl alcohol | 4 cc |
| Distilled $H_2O$ | 60 cc |
| Dioctyl sodium sulfosuccinate | 0.2 to 0.8 cc |
| 10% potassium hydroxide | 0.5 cc |

In this Example No. 4, no benzocaine is used and the ethyl alcohol is combined with dioctyl sodium sulfosuccinate and potassium hydroxide. This composition also reduces pain from sunburn.

EXAMPLE NO. 5

| | |
|---|---|
| Indomethacin | 0.083% by weight |
| Benzocaine | 0.5% by weight |
| Phenol (liquid) | 1.0% by weight |
| Ethyl alcohol | 4 cc |
| Cellosolve | 0.5 to 2.5% |
| Distilled H$_2$O | 60 cc |

In this composition, a solubilizing agent, Cello solve, is substituted for dioctyl sodium sulfosuccinate to help dissolve the indomethacin and the benzocaine in water.

This invention is intended to cover all changes and modifications of the example of the invention herein chosen for purposes of the disclosure which do not constitute departures from the spirit and scope of the invention.

What is claimed is:

1. A composition for treating sunburn comprising about 0.04% to about 2% by weight indomethacin, about 0.25% to about 1% by weight benzocaine, about 0.5% to about 2% by weight phenol, and an alcoholic and aqueous carrier.

2. The composition of claim 1 further comprising solubilizing agent.

3. The composition of claim 2 wherein the solubilizing agent is ethylene glycol monoethyl ether acetate.

4. A composition for treating sunburn comprising about 0.04% to about 2% by weight indomethacin, 10% potassium hydroxide solution, about 0.5% to about 2% by weight phenol and water.

5. The composition of claim 4 for treating sunburn further comprising a surfactant.

6. The composition of claim 5 wherein the surfactant is dioctyl sodium sulfosuccinate.

7. The composition of cliam 5 wherein the alcohol is ethyl alcohol.

* * * * *